United States Patent
Gecnuk

(10) Patent No.: US 9,575,024 B2
(45) Date of Patent: Feb. 21, 2017

(54) DECODER FOR DETERMINING A SUBSTANCE OR MATERIAL STRUCTURE OF A DETECTED OBJECT BASED ON SIGNALS OF A CAPACITIVE SENSOR AND METHOD FOR DETERMINING A SUBSTANCE OR MATERIAL STRUCTURE OF A DETECTED OBJECT BASED ON SIGNALS OF A CAPACITIVE SENSOR

(75) Inventor: Libor Gecnuk, Prostejov (CZ)

(73) Assignee: NXP USA, INC., Austin, TX (US)

( * ) Notice: Subject to any disclaimer, the term of this patent is extended or adjusted under 35 U.S.C. 154(b) by 451 days.

(21) Appl. No.: 13/877,176

(22) PCT Filed: Oct. 15, 2010

(86) PCT No.: PCT/IB2010/054685
§ 371 (c)(1),
(2), (4) Date: Apr. 1, 2013

(87) PCT Pub. No.: WO2012/049535
PCT Pub. Date: Apr. 19, 2012

(65) Prior Publication Data
US 2013/0314106 A1    Nov. 28, 2013

(51) Int. Cl.
G01R 27/26 (2006.01)
G01N 27/22 (2006.01)
G06F 3/041 (2006.01)
G06F 3/044 (2006.01)

(52) U.S. Cl.
CPC ............ *G01N 27/221* (2013.01); *G06F 3/044* (2013.01); *G06F 3/0416* (2013.01)

(58) Field of Classification Search
CPC ............ G01R 27/2605; G01R 31/028; G01R 31/2887; G01R 31/2831; G01R 31/312; G01R 31/08; G01R 31/2805; G01R 31/06794; G01D 5/24; G06K 9/0002; H03K 17/962; H03K 17/955
USPC ............ 324/750.17, 754.28, 519, 658–690; 345/173, 174; 178/18.01
See application file for complete search history.

(56) References Cited

U.S. PATENT DOCUMENTS

| 5,179,926 | A | 1/1993 | Ament |
| 5,694,046 | A * | 12/1997 | Hillerich et al. ............ 324/681 |
| 6,789,474 | B2 | 9/2004 | Wang |
| 6,857,313 | B2 | 2/2005 | Williamson |
| 7,260,987 | B2 | 8/2007 | Florenz |

(Continued)

FOREIGN PATENT DOCUMENTS

WO    2009058359 A1    5/2009

OTHER PUBLICATIONS

International Search Report and Written Opinion correlating to PCT/IB2010/054685 dated Jul. 8, 2011.

*Primary Examiner* — Son Le
*Assistant Examiner* — Thang Le

(57) ABSTRACT

A decoder unit for determining a substance or material structure of a detected object based on signals of a capacitive sensor comprises a distribution determination device arranged to determine a detected distribution relation based on signals of the at least one capacitive sensor; a comparison device arranged to compare the detected distribution relation with at least one predetermined distribution relation, the at least one predetermined distribution relation corresponding to a substance or a material structure and an output device arranged to indicate the result of the comparison carried out by the comparison device.

19 Claims, 4 Drawing Sheets

(56) References Cited

U.S. PATENT DOCUMENTS

| | | | |
|---|---|---|---|
| 7,616,011 B2 | 11/2009 | Zarabadi et al. | |
| 8,392,486 B2* | 3/2013 | Ing | 708/191 |
| 8,766,948 B2* | 7/2014 | Yanase | G06F 3/0416 |
| | | | 178/18.06 |
| 8,929,601 B2* | 1/2015 | Caulfield | H04N 5/30 |
| | | | 348/207.99 |
| 2003/0072475 A1* | 4/2003 | Tamori | 382/124 |
| 2008/0222827 A1* | 9/2008 | Veerasamy | B32B 17/10036 |
| | | | 15/250.12 |
| 2011/0074731 A1* | 3/2011 | Inoue et al. | 345/174 |
| 2011/0084936 A1* | 4/2011 | Chang et al. | 345/174 |
| 2011/0148438 A1* | 6/2011 | Dattalo | G06F 3/0416 |
| | | | 324/671 |
| 2011/0193571 A1* | 8/2011 | Lin et al. | 324/679 |

\* cited by examiner

DECODER FOR DETERMINING A SUBSTANCE OR MATERIAL STRUCTURE OF A DETECTED OBJECT BASED ON SIGNALS OF A CAPACITIVE SENSOR AND METHOD FOR DETERMINING A SUBSTANCE OR MATERIAL STRUCTURE OF A DETECTED OBJECT BASED ON SIGNALS OF A CAPACITIVE SENSOR

FIELD OF THE INVENTION

This invention relates to a decoder unit for determining a substance or material structure of a detected object based on signals of a capacitive sensor. It also pertains to a method for determining a substance or material structure of a detected object based on signals of a capacitive sensor and a related computer program product stored on a computer-readable medium.

BACKGROUND OF THE INVENTION

In many technical fields, capacitive sensors are used to detect the presence of certain substances. Generally, the capacitive sensor is arranged to measure a certain capacitance. If a substance is brought close to the sensor or in contact with the sensor, the dielectric conditions and the capacitance close to the sensor change, giving rise to a change in the capacitance value detected by the sensor. Based on the measured capacitance value, it thus is possible to e.g. detect the presence of fingertip brought close to the capacitors of the sensor. It is well known to use such capacitive sensors e.g. for the touch screen of computer terminal or a mobile device. Similarly, capacitive sensors are used e.g. as input devices for inductive heaters, e.g. modern cooking plates.

It is known from WO 2009/058359 A1 to use a plurality of capacitance sensors to determine the nature of a substance. The document U.S. Pat. No. 7,260,987 B2 describes the use of alternating voltage signals of differing frequencies for a capacitive fill level measurement.

SUMMARY OF THE INVENTION

The present invention provides a decoder unit for determining a substance or material structure of a detected object based on signals of capacitive sensor, a sensor arrangement comprising such a decoder unit, a method for determining a substance or material structure of a detected object based on signals of a capacitive sensor and a related computer program product according to the accompanying claims.

Specific embodiments of the invention are set forth in the dependent claims.

These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity.

DETAILED DESCRIPTION OF THE PREFERRED EMBODIMENTS

Figure 1:
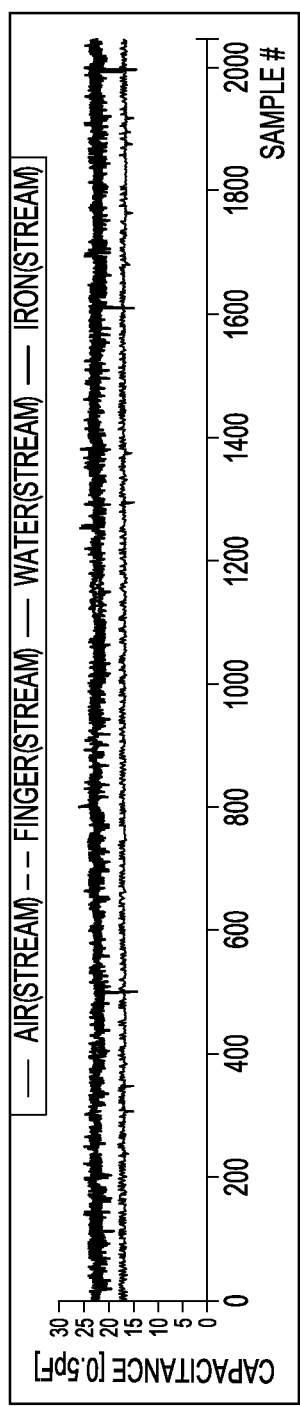
FIG. 1 shows a graph illustrating an example of capacitance values as sampled by a capacitive sensor for different substances.

Because the illustrated embodiments of the present invention may for the most part be implemented using electronic components and circuits known to those skilled in the art, details will not be explained in any greater extent than that considered necessary for the understanding and appreciation of the underlying concepts of the present invention and in order not to obfuscate or distract from the teachings of the present invention.

In the context of this specification, a capacitive sensor may be any kind of sensor which uses one or more capacitors to measure a capacitance at a certain point or in a given area or volume. A capacitive sensor may be arranged to sample a capacitance value at a given sampling frequency or sampling rate. The capacitive sensor may provide corresponding signals at a given rate, which may be equal to the sampling rate. A signal, or data based on a signal or signals, of the capacitive sensor may be provided to a decoder unit via a connection, which may be any kind of connection suitable for the transport of signals, e.g. a wire, optical cable or a wireless connection. Data based on the signals of the capacitive sensor may for example be derived directly from the signals, e.g. via an analog to digital conversion, or indirectly for example after processing the signals. Such processing can for example include any number and/or order of processes of filtering, packaging, sorting and/or transforming directly or indirectly signals or data based on signals. Processing may also include performing calculations directly or indirectly on signals or data based on signals.

A distribution relation may be any kind of distribution directly or indirectly based on signals of a capacitive sensor, in particular a distribution function. A distribution relation may be time-dependent or time-independent. A distribution relation may be determined by a transformation of signals or data based on signals into a suitable domain, e.g. the frequency or wavelength domain. A transformation may for example be achieved by using a Fourier transform, e.g. a fast fourier transform (FFT) or an inverse FFT (iFFT). A distribution relation may be considered to at least indicate a relation between a plurality of values of a first parameter, e.g. a capacitance, and a plurality of values of a second parameter, e.g. number of counts (e.g. counts of a capacitance value measured in a data stream) or samples.

A detection parameter may be any parameter indicative of a detection or non-detection of an object. Based on a detection parameter or on a comparison of a detection parameter with a baseline parameter, it may be possible to judge whether an object has been detected. For example, the averaged capacitance value be used as a detection parameter. A baseline parameter may e.g. an averaged capacitance measured without an object being detected. The presence of an object may be detecting by comparing a measured value for the detection parameter with a predetermined, e.g. fixed or time-varying, value of the baseline parameter.

A distribution relation may be predetermined, e.g. it may be determined experimentally and/or from theoretical models. The term distribution relation may generally indicate a detected distribution relation, which may determined based on signals of a sensor, and/or a predetermined distribution relation. For example, a predetermined distribution relation may indicate a distribution of capacitance values to be expected when an object of given substance or material structure, e.g. a finger, is brought close to a capacitive sensor. A distribution relation may be normalised. In particular, the distribution relations may be normalized, for ease of comparison. A predetermined distribution relation may indicate a characteristic structure or shape of a distribution relation of a substance or material structure. Distribution relations may be compared to each other in commonly known ways. It may be contemplated that a comparison of distribution relations may refer to a comparison of the shapes of the distribution relations. A comparison between distribution relations may involve the comparison and/or processing of at least a plurality of values of a first distribution relation with at least a plurality of values of a second distribution relation. It may be considered that extracting, e.g. by averaging, a single parameter value, e.g. a detection parameter, from a distribution relation and comparing it with a corresponding single parameter value of another distribution relation does not constitute a comparison of distribution relations in the sense used in this specification.

A substance may be of any kind of composition. It may be envisioned that a substance has a given chemical composition and may comprise one or more components. A material structure may be any structure comprising one or more substances, and has a given physical form or shape. It should be noted that the type of substance or the form of a material structure may influence measurements of capacitive sensors, owing to the tendency of substances and material structures to influence the dielectric characteristics and the capacitance of capacitors in their neighbourhood. A distribution relation corresponding to or associated with a substance or a material structure may be considered to be a distribution relation characteristic for the substance or the material structure.

Now turning to FIG. 1, there are shown time sequences of signals of a capacitive sensor for objects consisting of different substances brought close to the capacitive sensor. FIG. 1 shows the running number of a sample provided by the sensor on the horizontal axis, which thus represents a time axis, versus the measured capacitance in units of 0.5 pF. The measurement points represent streams of capacitance values The lowest line corresponds to capacitance values measured with no substance to be detected close to the sensor, e.g. only ambient air is measured. The thus measured values for air may be considered to be a baseline of the capacitive sensor representing a non-detection of an object. The upper curves correspond to streams of signals for detected objects, in this case a finger, water and an iron object brought close to the capacitive sensor. As shown in FIG. 1, the measured capacitance value increases roughly by 2.5 pF in absolute value for each of the streams related to a finger, water and the iron object. It is noted that the signal is highly volatile and shows complex time structures due to the high sensitivity of the capacitive sensor, which strongly react even to small changes in environment and may be influenced by the exact nature of the substance and/or material structure detected, for example by its form or shape. Also, movement of the detected object and/or an influx of air or breath may influence the temporal structure of the signal. For this reason, a low-pass filtering may be performed on the streams before averaging the measured values to obtain an average capacitance value which may be attributed to the substance brought close to the sensor. Thus, based on the processed signals it may be concluded that a detection of an object occurred if the absolute capacitance value changed compared to the baseline. It may be feasible to consider a change in capacitance instead of an absolute averaged value for detection. It may be envisioned to provide one or more absolute capacitance values or values derived from such capacitance values as indicators or detection parameters for a detection. Instead of, or additional to averaging, one or more different methods of determining an absolute value as indicator or detection parameter for object detection may be utilized.

As illustrated in FIG. 1, that an object is present can be determined but the absolute capacitance value or changes over the baseline do not reveal information about the specific substances or material structures of a detected object based on such. In particular, the signals do not differentiate between a human finger, a drop of water or e.g. an iron pot caused the increase in measured capacitance from the absolute averaged capacitance value or the capacitance value increase alone.

Figure 6:
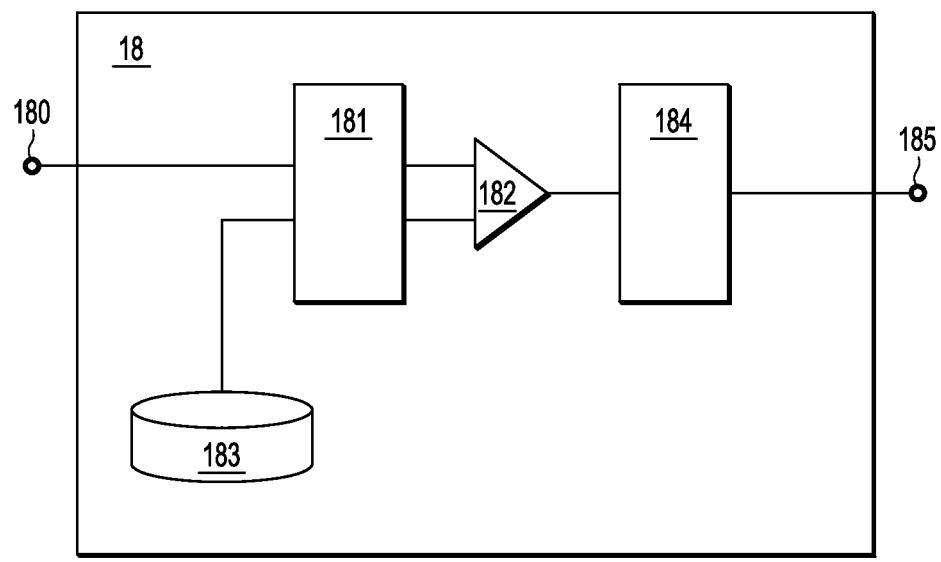
FIG. 6 shows a block diagram of an example of an embodiment of a decoder unit.

As illustrated in FIG. 6, a decoder unit 18 may be used to determine which substance or material structure is present based on signals of a capacitive sensor. The decoder unit 18 may include a distribution determination device 181 arranged to determine a detected distribution relation based on signals of the at least one capacitive sensor, for example received at an input 180 of the decoder unit 18 to which the device 181 is connected. The distribution determination device provides may, if so desired, determine a plurality of different distribution relations based on the same signals. For example, distribution relations indicating relations between differing parameters and/or time-dependent and time-independent distribution relations may be provided. A distribution relation may be a representation of a histogram. A histogram may indicate the number of samples falling into a given range of measured capacitance values. It may be feasible that a distribution relation indicating a number of samples of a given measured capacitance value and/or a distribution relation indicating a frequency distribution of the signals (e.g. using a Fourier transform) and/or a cepstrum are provide as distribution relations. The samples under consideration may be taken over a given time. It may be feasible that the distribution determination device is arranged to select samples from a stream of samples according to predetermined criteria, e.g. based on a change of average measured values. Any of the distribution relations may be time-independent or a time-dependent.

The decoder unit 18 may comprise a comparison device 182 connected to the distribution determination device 181 and arranged to compare the detected distribution relation with at least one predetermined distribution relation. The predetermined distribution relation may for example have been determined prior to the comparison by the comparison device 182 and be stored in a memory 183 connected to the comparison device 182.

The at least one predetermined distribution relation may correspond to a substance or a material structure. Two compared distribution relations may be considered to be equal if predefined criteria are fulfilled. For example, there may be defined maximum deviation values between the compared distribution relations within which they are considered to be matching or equal. If two compared distribution relations are judged to be equal or to match, the substance or material structure of the detected object, as represented by the detected distribution relation, may be determined to be equal to the substance or material structure associated with the predetermined distribution relation of the comparison. Distribution relations corresponding to a plurality of substance and/or material structures may be provided. A plurality of different predetermined distribution relations are provided for a given or any number of substances or material structures. A plurality of detected distribution relations may be compared to corresponding predetermined distribution relations. The comparison device may be arranged to judge whether distribution relations match or are equal. It may be contemplated to arrange the comparison device to provide an indication whether a match occurred and/or with which predetermined distribution relation the match occurred and/or for which substance or material structure a match occurred. Such an indication may e.g. be provided to any other device of the decoder unit 18 and/or to an external device.

The decoder unit 18 may comprise a calculation device arranged to calculate an object detection parameter value based on signals of at least one capacitive sensor. The detection parameter value may e.g. be a capacitance value. The detection parameter value may e.g. represent a change in measured values, which may indicate the presence of an object in a detection region of the sensor. The calculation device may process the signals or data, in particular it may filter the signals or data based on the signals.

It may e.g. be envisioned that the calculation device provides an average value of measured capacitance values as a capacitance value. Averaging of measured values may be performed after filtering. Filtering may be a low-pass filtering to filter out high-frequency noise signals. It may be considered that the calculation device is arranged to indicate a detection of an object. A detection may be indicated e.g. if a change in the capacitance value over a baseline value is detected. It may be considered that a detected distribution relation is only determined if the calculation device indicates a detection. For that purpose, a detection parameter or detection signal may be provided by the calculating device. A detection parameter or detection signal may be provided to an electronic control device and/or a software control and/or to the distribution relation determination device. In the shown example, the calculation device is integrated with the distribution relation determination device. However, (parts of) the calculation device may alternatively or additionally, be integrated in other parts of the decoder unit. For example, a separate calculation device may be present upstream of the device 181 and down-streams of the input 180 which can provide an activation signal to the distribution determination device 181 in response to detecting an object. It may be considered that the determination of a detected distribution relation is performed based on a first set of data based on sensor signals, which differs from a second set of data, based on the sensor signals, the detection parameter is calculated from. It may be feasible that e.g. the first set of data is preprocessed differently than the second set of data.

There may be provided an output device 184 connected to the comparison device 183 arranged to indicate the result of the comparison carried out by the comparison device. The output device may be arranged to indicate whether a substance has been identified and/or one or more distribution relations and may output data representing such information at an output 185 of the unit 18. The output device 184 may be connected via the output 185 to communicate control signals and/or data to the distribution relation determination device and/or the calculation device and/or a control device which controls another device based on the received information. The output device may be part of the decoder unit and/or the distribution relation determination device and/or the calculation device. The output device may be implemented comprising a connection for transmitting signals and/or data. The output device may comprise or represent an interface and/or a software interface.

The devices mentioned above may be provided in software, hardware and/or firmware. It may be feasible to provide one or more devices separately or as integrated device. Suitable interfaces allowing communication between devices may be provided.

The decoder unit 18 may be connected or connectable to at least one capacitive sensor 12. It may be considered that the decoder unit comprises at least one sensor. The decoder unit may be considered to be separate from the sensor. It may be envisioned that the decoder unit is connected or connectable to at least one transmitter. The at least one transmitter may be arranged to transmit electromagnetic signals at one or more frequencies. It may be considered that the at least one transmitter transmits the signals into the measurement or detection region of the capacitive sensor. By providing a signal with a transmitter, it is possible to induce reactions in objects which may be visible in the detected distribution relation. For example, the human body responds to electromagnetic radiation in a way which may be recognized in a signal of a capacitive sensor if a body part, e.g. a finger, is detected. It may be considered to choose a signal frequency of the transmitted signals to provide an easily recognized characteristic in a detected distribution relation. To this purpose, it may be determined experimentally which kind of substance or material structure shows a characteristic structure in a distribution relation for a given frequency. A corresponding detected distribution relation may be determined, in particular by the distribution relation determination device. It may be considered to provide one or more corresponding predetermined distribution relations, which may take into account the transmitted frequencies and the corresponding responses of substances or material structures. It is feasible to transmit a signal having a commonly used frequency, which usually contributes to a background radiation. For example, the at least one transmitter may be arranged to transmit an electromagnetic signal having a frequency between 25 and 100 Hz, preferably between 50 and 60 Hz. Alternatively or additionally, the at least one transmitter may be arranged to transmit an electromagnetic signal having a frequency of approximately 2 kHz. The transmitter may be controlled by an electronic control device and/or software. It may be contemplated that the decoder unit is arranged to control the transmitter. The distribution relation may correspond to a human finger and/or water and/or iron.

A sensor arrangement comprising at least one capacitive sensor connected to a decoder unit as described above may be considered. The sensor arrangement may comprise at least one transmitter as mentioned above. It may be feasible to provide a mobile device or a computing device with such a sensor arrangement. A touch screen having such a sensor arrangement may be provided, e.g. for a mobile device and/or a computer and/or a terminal. The sensor arrangement and/or decoder unit is also particularly well suited for use as an input device for an inductive cooking device.

A method for determining a substance or material structure of a detected object based on signals of a capacitive sensor may be considered. The method may be performed with any of the devices described above and may comprise any feature described with regard to these devices. The method may comprise providing at least one predetermined distribution relation corresponding to a substance or material structure as described above. Determining a detected distribution relation based on signals of the at least one capacitive sensor may be performed. The detected distribution relation may be compared with the predetermined distribution relation. As described above, any number of distribution relations may be determined and/or any number of predetermined distribution relations may be provided. It may be considered that the method comprises calculating a detection parameter based on signals of at least one capacitive sensor.

It may be determined that a substance or material structure of an object has been detected based on the result of comparing the data information structure and/or the detection parameter.

The detected distribution relation may comprise a time-independent distribution of measured values. The method may include transmitting an electromagnetic signal having a predetermined frequency.

Figure 2:
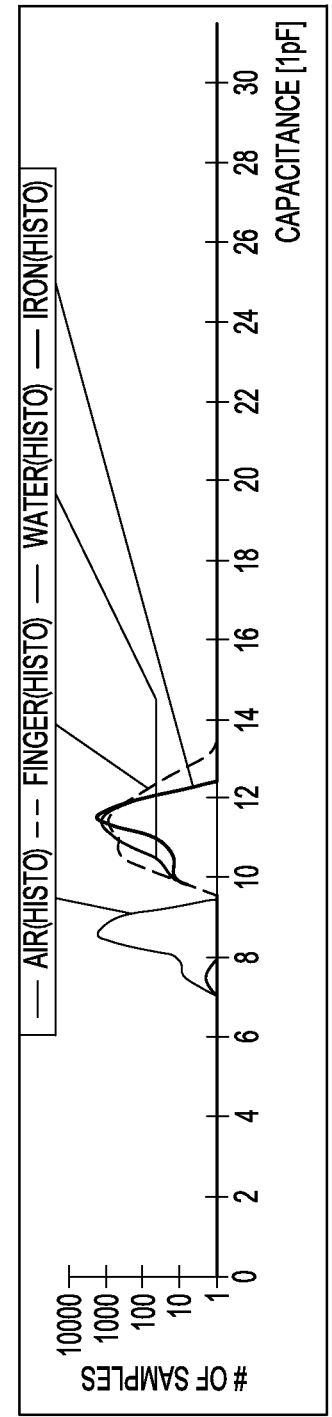
FIG. 2 shows a graph illustrating an example of a shape of distribution of measured capacitance values.

FIG. 2 shows an example of a distribution function of a number of samples measured for a given capacitance value (in units of 1 pF) provided by a data stream within a certain time. Thus, the distribution function in FIG. 2 may be considered to be time-independent. As may be seen for air, e.g. no object to be detected, the distribution peaks around 9 pF and has a slight secondary peak on its lower value flank. For water, iron and the human finger, the distribution functions peak around a value of 11.5 pF, roughly 2.5 pF higher than for air. The peak values essentially are identical for finger, water and iron. Thus, based upon the peak value of the measured capacitance, which roughly corresponds to the average value, it may not be possible to tell whether a finger, water or iron has been detected. However, the shapes of the distribution functions differ significantly. This may be seen in closer detail from FIG. 3, which shows in its lower panel the distribution function of FIG. 2 and, in its upper panel, a delta-noise graph of the same distribution in which the value of a measured capacitance for a given sample is subtracted from the capacitance value measured for the following sample to provide a normalized representation centered around a capacitance of 0. This normalization may be considered to lead to a symmetrisation of the shape of the distributions. It is possible to directly compare the shape of the baseline (air) with the shape of the distribution functions for different substances measured. As can be seen, significant side peaks appear for water at −4 pF and 4 pF, which do not appear for other substances. Side structures appear for iron at approximately −1.8 pF and 1.8 pF. For the human finger, the shape of the distribution function may be identified as being broader and having a characteristic skewedness, which can be seen particularly well from the lower panel of FIG. 3. Thus, the shapes of the distribution functions significantly vary even for comparable average capacitance values measured by a capacitive sensor. Based on this consideration, it is possible to identify the substance or material structure of the detected object. It may be considered to provide suitable predetermined distribution relations for the substance or material structures of objects whose detection is desired, e.g. for a human finger or a pen, to enable a comparison and subsequent identification or determination of the substance or material structure.

Figure 3:
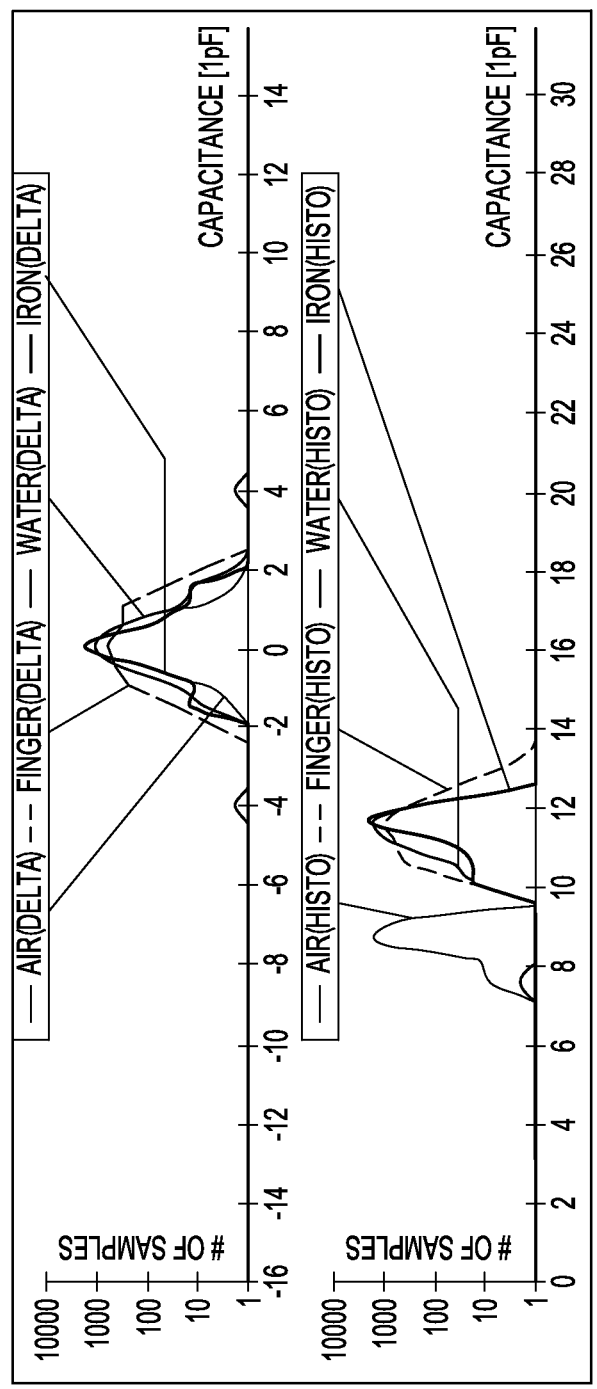
FIG. 3 shows a graph illustrating data information structures without an external modulation frequency.
Figure 4:
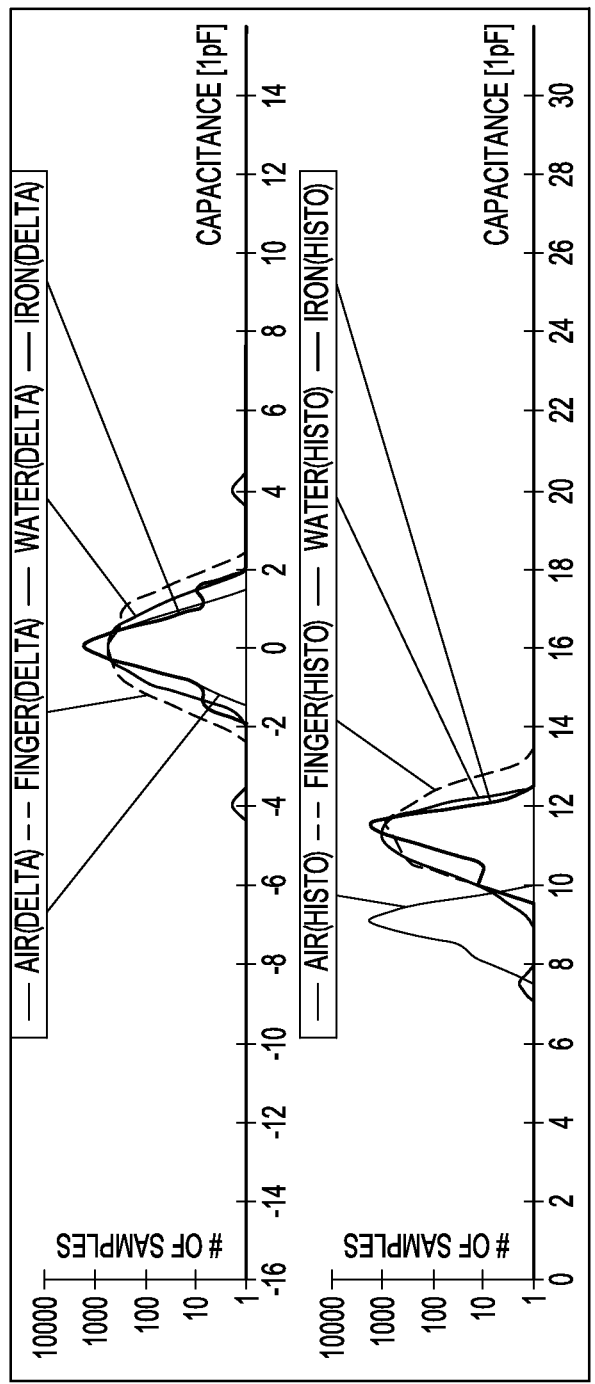
FIG. 4 shows a graph illustrating data information structures with an external modulation frequency.

FIG. 4 shows distribution functions similar to those shown in FIG. 3. For the measurements shown in FIG. 4, a 50 Hz external signal was present as it might occur, e.g. in a room with an electrical outlet. It may be recognized from FIG. 4 that the signal influences the shape of the distribution functions, but leaves the idiosyncrasies of each curve in place. For a human finger, iron, and water, the identity of the substance or material structure may thus be determined robustly, even in the presence of such an external signal. It may be feasible to provide a defined external signal to increase the sensitivity of detection and/or to ensure that measurements occur in comparable environments.

Figure 5:
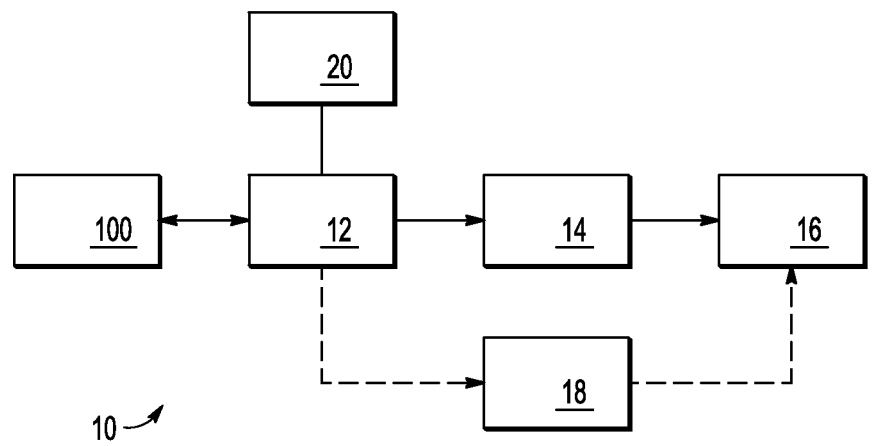
FIG. 5 shows a block diagram of an example of a capacitive sensor system

FIG. 5 shows an example of a sensor system 10, for example a touch sensing system. Sensor system 10 may comprise a capacitive sensor 12 or be connectable thereto. The capacitance measured by sensor 12 may be influenced by the environment 100. In particular, the capacitance values measured depend on whether an object is brought into the close environment 100 and its substance and/or material structure. The sensor 12 may be connected to a signal processing device 14. The signal processing device 14 may be provided with sample signals by sensor 12 and may perform low-pass filtering of this raw data. In addition, the signal processing device 14 may provide a detection parameter, e.g. an absolute capacitance value, based on the samples provided by the sensor 12. The signal processing device 14 may be considered as a calculation device as described above. The absolute capacitance value, which may be an averaged value of capacitance measure by the sensor 12 over a given time, or may represent a difference between a measured capacitance value and a baseline value, may be provided to a touch detection device 16. It may be considered that signal processing device 14 indicates the detection of an object to touch detection device 16 and/or to further devices. Touch detection device 16 may e.g. be a customized application running on a microprocessor system.

Raw signal data from sensor 12 may also be provided to a substance decoding device 18. It may be considered that the substance decoding device 18 is provided with a preprocessed set of data based on sensor signals. Data may be provided by the sensor or a device arranged to preprocess and/or transmit or distribute sensor signals. It is feasible that the data or signals are provided by the signal processing device 14. Substance decoding device 18 may be implemented in the same device as the signal processing device 14, or it may be a physically separate device. Substance decoding device 18 may be seen as a decoder unit or part of a decoder unit described above. It may comprise a reception device arranged to receive the signals or data. Substance decoding device 18 may comprise or represent a distribution relation determination device arranged to determine a detected distribution relation based on signals of sensor 12, e.g. based on a preprocessed set of data or directly on sensor signals. For example, decoding device 18 may be arranged to provide a time-independent detected distribution relation of measured capacitance values and/or may be arranged to provide a time-dependent detected distribution relation of measured capacitance values. As a result, it may provide and/or determine a detected distribution relation of any suitable parameters, like e.g. capacitance, time, frequency, etc. The decoding device 18 may comprise or represent a comparison device arranged to compare the detected distribution relation with at least one pre-determined distribution relation. The at least one pre-determined distribution relation may correspond to a substance or material structure. For example, the predetermined distribution relation may indicate a parameter relation of water, a finger, iron or any other substance.

It is feasible to provide the predetermined distribution relation in the same form or format as the detected distribution relation determined. It may be envisioned to provide a predetermined distribution relation in a different format. In this case, it may be considered to transform the detected distribution relation and/or the predetermined distribution relation to be able to compare them. The comparison device may be arranged to compare the detected distribution relation with the at least one predetermined distribution relation There may be provided an output device arranged to indicate the result of the comparison. The result may indicate the identification of a given substance or may provide other data based on the comparison. It may be feasible that the result of the comparison is provided to the touch detection device 16 by the output device.

Touch detection device 16 may be arranged to receive data from the signal processing device 14 and the substance decoding device 18. It may be arranged to determine and/or indicate the detection of an object and the determination of its substance or material structure based on signals or data received from signal processing device 14 and/or substance decoding device 18. It may be considered that touch detection device 16 receives an indication that an object has been detected from signal processing device 14. It is feasible that the touch detection device 16 is arranged to instruct substance decoding device 18 to determine a detected distribution relation and to perform a comparison only if it receives information indicating a detection of an object from signal processing device 14. Signal processing device 14 may be arranged to directly instruct substance decoding device 18 correspondingly. It may be considered that sensor system 10 comprises a transmitter 20. The transmitter 20 may be arranged to transmit an electromagnetic signal of a given frequency. The frequency may be in a range between 25 and 100 Hz and may preferably lie between 50 and 60 Hz. Alternatively or additionally, transmitter 20 may be arranged to transmit an electromagnetic signal having a frequency in a different frequency range or ranges. A frequency range may correspond to a range commonly used for directly measured bioimpedance analyses, e.g. of the human body. Such a frequency or frequency range may be used to achieve an indirect measurement utilizing the capacitive sensor and/or decoder unit. A utilized frequency may lie in the kHz and/or tens of kHz range. A utilized frequency or frequency range may for example be approximately 2 kHz, 6 kHz and/or 60 kHz. Signal processing device 14 and/or substance decoding device 18 and/or touch detection device 16 may be implemented in software running on a computer. There may be provided interfaces suitable for communication between the devices, in particular software interfaces.

The invention provides the possibility to determine the substance or material structure of an object detected by a capacitive sensor. It enables to distinguish between different substances or material structures. For example, it may be distinguished whether an input to a touch screen originated from a human finger or occurred accidentally by an object getting into contact with a touch screen. The invention is also particular suitable for distinguishing inputs to a control of an inductive cooking device, as the electromagnetic environment of such a device is usually particularly noisy. However, the invention may be used in any device or environment in which a capacitive sensor is used to distinguish substances, material structures and shapes. It may be feasible to provide suitable predetermined distribution relations depending on the kind of substances and/or material structures of the objects to be detected. It is possible to upgrade a sensor system already in place with the decoder unit to enable determination of different substances or material structures. In particular, a computing system connected to a sensor may be easily upgraded with a software implementation of the invention without the need to provide additional hardware.

The invention may be implemented in a computer program for running on a computer system, at least including code portions for performing steps of a method according to the invention when run on a programmable apparatus, such as a computer system or enabling a programmable apparatus to perform functions of a device or system according to the invention. In particular, the invention may be implemented as a computer program product stored on a computer-readable medium comprising the features of one of the decoder units described above and/or arranged to perform one of the methods described above.

A computer program or a computer program product is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program or computer program product may be stored internally on computer readable storage medium or transmitted to the computer system via a computer readable transmission medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc.; and data transmission media including computer networks, point-to-point telecommunication equipment, and carrier wave transmission media, just to name a few.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

The invention may be implemented at least partly as an integrated circuit on a semiconductor substrate. For example, the semiconductor substrate described herein can be any semiconductor material or combinations of materials, such as gallium arsenide, silicon germanium, silicon-on-insulator (SOI), silicon, monocrystalline silicon, the like, and combinations of the above.

The connections or interfaces as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality. For example, the sensor may be connected to the calculation device and/or the distribution relation determination device and/or a preprocessing device arranged to preprocess signals from the sensor and/or distribute data based on the signals from the sensor to the calculation device and/or the distribution relation determination device.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. For example, the calculation device and the distribution relation determination device may be provided in a single device. Alternatively, the examples may be implemented as any number of separate integrated circuits or separate devices interconnected with each other in a suitable manner. For example, the calculation device and/or the distribution relation determination device and/or the output device may be separate devices or circuits.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

In the foregoing specification, the invention has been described with reference to specific examples of embodiments of the invention. It will, however, be evident that various modifications and changes may be made therein without departing from the broader spirit and scope of the invention as set forth in the appended claims.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements The mere fact that certain measures are recited in mutually different claims does not indicate that a combination of these measures cannot be used to advantage.

The invention claimed is:

1. A decoder unit for determining a material of a detected object based on a signal from a capacitive sensor, the decoder unit comprising:
   a distribution determination device that determines a detected distribution relation based on the signal;
   a comparison device that compares the detected distribution relation with a first predetermined distribution relation of a plurality of predetermined distribution relations and with a second predetermined distribution relation of the plurality of predetermined distribution relations, the first predetermined distribution relation being associated with a first material and the second predetermined distribution relation being associated with a second material; and
   an output device that indicates the presence of the first material and indicates a first detected object as accidentally contacting the capacitive sensor when the detected distribution relation matches the first predetermined distribution relation, and that indicates the presence of the second material and indicates a second detected object as intentionally contacting the capacitive sensor when the detected distribution relation matches the second predetermined distribution relation.

2. The decoder unit according to claim 1, wherein the detected distribution relation comprises a time-independent distribution of measured values.

3. The decoder unit according to claim 1, wherein the decoder unit is connected to a capacitive sensor.

4. The decoder unit according to claim 1, wherein the decoder unit is connected to a transmitter that provides the signal.

5. The decoder unit according to claim 4, wherein the signal comprises an electromagnetic signal having a frequency between 25 and 100 Hz.

6. The decoder unit according to claim 4, wherein the signal comprises an electromagnetic signal having a frequency of approximately 2 kHz.

7. The decoder unit according to claim 1, wherein the first predetermined distribution relation corresponds to one of a human finger, water, and iron.

8. The decoder unit according to claim 1, wherein the distribution determination device further receives an indication that the signal indicates the detection of the first object, and wherein determining the detected distribution relation is in response to the indication.

9. The decoder unit according to claim 1, further comprising:
a memory that stores the plurality of predetermined distribution relations.

10. The decoder unit according to claim 1, wherein:
the comparison device further compares the detected distribution relation with a second predetermined distribution relation of the plurality of predetermined distribution relations, the second predetermined distribution relation being associated with a second material;
the output device further indicates the presence of the second material when the detected distribution relation matches the second predetermined distribution relation.

11. The decoder unit according to claim 10, wherein the output device further indicates a second detected object as intentionally contacting the capacitive sensor when the detected distribution relation matches the second predetermined distribution relation.

12. A method for determining a material of a detected object based on a signal of a capacitive sensor, comprising:
providing a first predetermined distribution relation and a second predetermined distribution relation of a plurality of predetermined distribution relations, the first predetermined distribution relation corresponding to a first material and the second predetermined distribution relation corresponding to a second material;
determining a detected distribution relation based on the signal;
comparing the detected distribution relation with the first predetermined distribution relation;
indicating the presence of the first material when the detected distribution relation matches the first predetermined distribution relation;
indicating a first detected object as accidentally contacting the capacitive sensor when the detected distribution relation matches the first predetermined distribution relation;
comparing the detected distribution relation with the second predetermined distribution relation;
indicating the presence of the second material when the detected distribution relation matches the second predetermined distribution relation; and
indicating a second detected object as intentionally contacting the capacitive sensor when the detected distribution relation matches the second predetermined distribution relation.

13. The method according to claim 12, wherein the detected distribution relation comprises a time-independent distribution of measured values.

14. The method according to claim 12, further comprising:
transmitting the signal as an electromagnetic signal having a predetermined frequency.

15. The method according to claim 12, further comprising:
receiving an indication that the signal indicates the detection of an object, wherein determining the detected distribution relation is in response to the indication.

16. The method of claim 12,
comparing the detected distribution relation with a second predetermined distribution relation of the plurality of predetermined distribution relations, the second predetermined distribution relation corresponding to a second material; and
indicating the presence of the second material when the detected distribution relation matches the second predetermined distribution relation.

17. The method according to claim 16, further comprising:
indicating a second detected object as intentionally contacting the capacitive sensor when the detected distribution relation matches the second predetermined distribution relation.

18. A non-transitory computer-readable medium including code for performing a method, the method comprising:
providing a first predetermined distribution relation and a second predetermined distribution relation of a plurality of predetermined distribution relations, the first predetermined distribution relation corresponding to a first material and the second predetermined distribution relation corresponding to a second material;
determining a detected distribution relation based on a signal of a capacitive sensor;
comparing the detected distribution relation with the first predetermined distribution relation;
indicating the presence of the first material when the detected distribution relation matches the first predetermined distribution relation;
indicating a first detected object as accidentally contacting the capacitive sensor when the detected distribution relation matches the first predetermined distribution relation;
comparing the detected distribution relation with the second predetermined distribution relation;
indicating the presence of the second material when the detected distribution relation matches the second predetermined distribution relation; and
indicating a second detected object as intentionally contacting the capacitive sensor when the detected distribution relation matches the second predetermined distribution relation.

19. The non-transitory computer-readable medium according to claim 18, the method further comprising:
receiving an indication that the signal indicates the detection of an object, wherein determining the detected distribution relation is in response to the indication.

* * * * *